Feb. 11, 1941. S. POULSEN Plant Pat. 446
ROSE PLANT
Filed Oct. 8, 1940
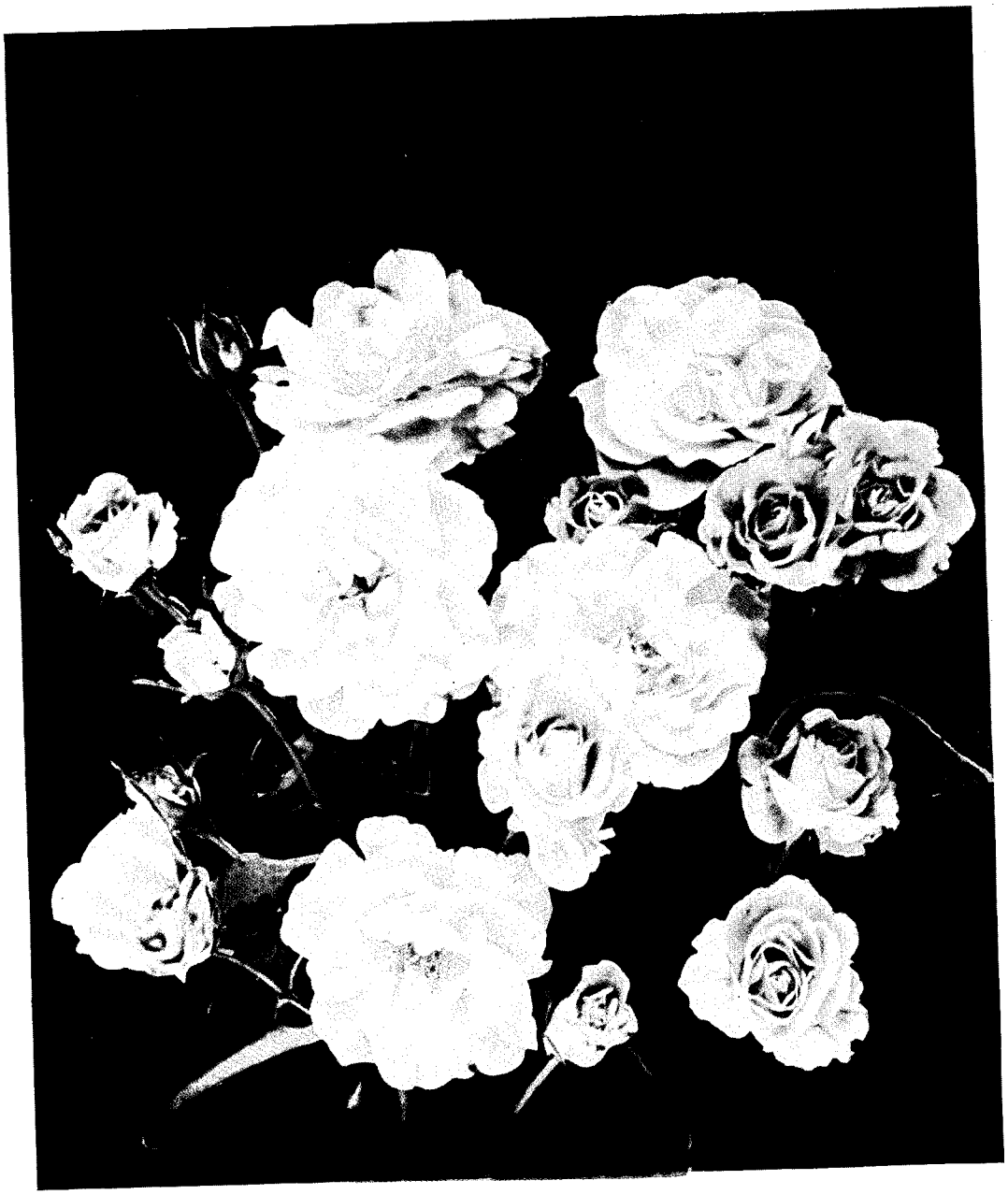
Inventor
S. Poulsen
By Robb & Robb
Attorneys Patented Feb. 11, 1941

Plant Pat. 446

UNITED STATES PATENT OFFICE

446

ROSE PLANT

Svend Poulsen, Copenhagen, Denmark, assignor to
The Conard-Pyle Company, West Grove, Pa.

Application October 8, 1940, Serial No. 360,329

1 Claim. (Cl. 47—61)

The present invention relates to a new and distinct variety of hybrid polyantha rose plant and is the result of the crossing of two dominant varieties, Ellen Poulsen of the polyantha type and Mevrouw G. A. van Rossem of the hybrid tea type.

The hybridizing of these two known varieties has produced what I consider to be an entirely new combination of colors on a plant characterized by its vigor of growth, shapeliness, abundance and persistence of bloom, all of which establishes this new variety as a most useful and decorative plant for garden purposes, particularly in view of its hardiness, bushy form, and free, continuous blooming in attractively colored clusters.

The following is a detailed description of this new rose, the color terminology employed therein being in accord with Ridgway's Color Standard:

Type: Hardy; tall bush; outdoor; for garden decoration.

Class: Hybrid polyantha.

Parentage:

*Seed parent.*—Ellen Poulsen.

*Pollen parent.*—Mevrouw G. A. van Rossem.

Propagation: Holds its distinguishing characteristics through succeeding propagations by budding.

*Flower*

Locality where grown: West Grove, Pennsylvania.

Flowers borne: In irregular clusters.

Quantity of bloom: Free outdoors.

Continuity. Continuous.

Fragrance: Slight; spicy.

Bud:

*Peduncle.*—Medium length; slender; medium stiff; Courge Green, Plate XVII; almost smooth; few hairs, Hays Maroon, Plate XIII.

*Before calyx breaks.—Size*—small. *Form*—Short, pointed, with foliaceous appendages on the surface of the bud, with slender bristle-like foliaceous parts extending beyond the tip of the bud equal to ½ to ¾ of its length.

*As calyx breaks.—Color*—clear dull Green Yellow, Plate XVII, marked with Garnet Brown, Plate I.

*As first petal opens.—Size*—small. *Form*—short, flat. *Color*: outside—Pinard Yellow, Plate IV, flushed with Rose Pink, Plate XII; inside—Barium Yellow base, Plate XVI, extending to Rose Pink flushed with Rose color, Plate XII.

*Opening.*—Opens up well.

Bloom:

*Size, when fully open.*—Medium; three inches to three and one-half inches.

*Petalage.*—Double with stamens showing; from twenty-five to thirty-five petals, arranged regularly.

*Form.*—Cupped at first, becoming open; petals at first very tightly rolled outward; becoming later, at maturity, very loosely rolled outward.

Petals: Thin, leathery, with inside and outside satiny.

*Shape.*—Outside—oval, scalloped with two notches. Intermediate—obovate, scalloped with one notch. Inside—linear, with apex flat.

This description of a newly opened flower was made from a rose grown outdoors, in October, 1939, at West Grove, Pennsylvania:

*Color.*—Outside petal: outside surface—Amber Yellow base, Plate XVI, extending to Alizarine Pink, Plate XIII; inside surface—Tyrian Rose, Plate XII, to Rose Color, Plate XII. Intermediate petal: outside surface—Amber Yellow base, Plate XVI, extending to Alizarine Pink, Plate XIII; inside surface—Tyrian Rose, Plate XII, to Rose Color, Plate XII. Inner petal: outside surface—Amber Yellow base, Plate XVI, extending to Alizarine Pink, Plate XIII; inside surface—Tyrian Rose, Plate XII, to Rose Color, Plate XII.

This description was made from a rose that was open for three days outdoors, in October, 1939, at West Grove, Pennsylvania:

*Color.*—Outside petal: outside surface—Pale Yellow Orange, Plate III, flushed with Rose Pink, Plate XII; inside surface—Rose Pink, Plate XII, lightly veined with Tyrian Pink, Plate XII. Inside petal: outside surface—Pale Yellow Orange, Plate III, flushed with Rose Pink, Plate XII; inside surface—Rose Pink, Plate XII, lightly veined with Tyrian Pink, Plate XII.

*General color effect.*—Newly opened flower—Deep Rose Pink, Plate XII. Three days open—Rose Pink, Plate XII.

*Behavior.*—Drop off cleanly; fading Rose Pink, Plate XII.

*Flower longevity.*—On bush in garden, three to four days in September; as cut roses from four to five days in October.

*Reproductive organs*

Stamens: Medium number, mixed with petaloids.
Filaments: Few without anthers; Pinard Yellow, Plate IV.
Anthers: Small; open at various times; Raw Sienna, Plate III.
Pollen: Moderate; Orange Buff, Plate III.
Pistils: Medium number.
Styles: Uneven; medium length; medium heavy; bunched.
Stigma: Light Orange Yellow, Plate III.
Ovaries: All enclosed in calyx.
Hips: Short; globular with inconspicuous neck; Cerro Green, Plate V; moderately smooth, walls thin.
Sepals: Falling soon; moderately long; recurved.
Seeds: Few; medium size.

*Plant*

Foliage:
*Leaves.*—Compound of three to seven; abundant; medium size; soft.
*Leaflets.*—Linear with apex acute; base round; margin simply serrate.
*Color.*—*Mature:* upper surface—Elm Green, Plate XVII; under surface—Light Hellebore Green, Plate XVII. *Young:* upper surface—Oil Green, Plate V; under surface—Lettuce Green, Plate V, flushed with Argus Brown, Plate III.
*Rachis.*—(The supporting stem of the compound leaf), medium heavy. Upper side—smooth, grooved; under side—sparsely thorny.
*Stipules.*—Medium long; medium wide, with medium points, turning out at an angle of more than 45°.
*Disease.*—Subject to blackspot.

Growth:
*Habit.*—Bushy, much branched.
*Growth.*—Free.
*Canes.*—Medium heavy.
*Main stems.*—Cerro Green, Plate V. *Thorns*—medium long, hooked downward with short, narrow base. *Prickles*—none. *Hairs*—none.
*Branches*—Cerro Green, Plate V, dull. *Thorns*—several; medium long, hooked downward with short, narrow base. *Prickles*—none. *Hairs*—none.
*New Shoots.*—Dull Olive Citrine, Plate XVI, overlaid with Hessian Brown, Plate XIII. *Thorns*—several; medium long, hooked downward with short, narrow base. *Prickles*—none. *Hairs*—none.

I claim:

A new and distinct variety of rose plant of the polyantha type, characterized as to novelty by its vigorous habit of shapely, bushy growth, its abundance and persistence of bloom in a novel combination of colors especially adapting it for decorative garden purposes, substantially as shown and described.

SVEND POULSEN.